United States Patent
Rahmel et al.

(10) Patent No.: US 9,693,955 B2
(45) Date of Patent: Jul. 4, 2017

(54) HUMIDIFIED PARTICLES COMPRISING A THERAPEUTICALLY ACTIVE SUBSTANCE

(75) Inventors: Daniela Rahmel, Hamburg (DE); Friedemann Taut, Constance (DE); Christian De Muynck, Constance (DE); Markus Rast, Radolfzell (DE); Peter Iwatschenko, Eckenthal (DE); Gerhard Pohlmann, Meerbeck (DE); Wolfgang Koch, Steimbke (DE); Horst Windt, Burgwedel (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 194 days.

(21) Appl. No.: 13/817,173

(22) PCT Filed: Aug. 22, 2011

(86) PCT No.: PCT/EP2011/064399
§ 371 (c)(1),
(2), (4) Date: Feb. 15, 2013

(87) PCT Pub. No.: WO2012/025496
PCT Pub. Date: Mar. 1, 2012

(65) Prior Publication Data
US 2013/0142782 A1    Jun. 6, 2013

(30) Foreign Application Priority Data

Aug. 23, 2010  (EP) .................................... 10173759

(51) Int. Cl.
| | | |
|---|---|---|
| A61K 9/12 | (2006.01) | |
| A61K 9/14 | (2006.01) | |
| A61K 9/00 | (2006.01) | |
| A61M 15/00 | (2006.01) | |
| A61M 16/10 | (2006.01) | |
| A61M 16/06 | (2006.01) | |
| A61M 16/16 | (2006.01) | |
| A61M 11/00 | (2006.01) | |
| A61M 16/14 | (2006.01) | |

(52) U.S. Cl.
CPC ............ *A61K 9/122* (2013.01); *A61K 9/0073* (2013.01); *A61K 9/0075* (2013.01); *A61K 9/0082* (2013.01); *A61M 11/003* (2014.02); *A61M 15/00* (2013.01); *A61M 15/009* (2013.01); *A61M 16/1065* (2014.02); *A61M 11/002* (2014.02); *A61M 16/0666* (2013.01); *A61M 16/142* (2014.02); *A61M 16/16* (2013.01); *A61M 2205/505* (2013.01); *A61M 2205/7518* (2013.01); *Y10T 137/0318* (2015.04)

(58) Field of Classification Search
CPC .. A61K 9/0073; A61K 9/0075; A61K 9/0082; A61K 9/122; A61M 15/00
See application file for complete search history.

(56) References Cited

U.S. PATENT DOCUMENTS

| | | | |
|---|---|---|---|
| 4,773,410 A | 9/1988 | Blackmer et al. | |
| 5,005,569 A | 4/1991 | Pasternack | |
| 5,299,566 A * | 4/1994 | Davis ................... | A61K 9/0078 128/200.14 |
| 5,874,406 A | 2/1999 | Schafer et al. | |
| 5,906,201 A | 5/1999 | Nilson | |
| 6,315,983 B1 | 11/2001 | Eistetter | |
| 6,712,881 B2 * | 3/2004 | Hering et al. ................... | 95/228 |
| 7,097,827 B2 * | 8/2006 | Platz .................... | A61K 9/0075 424/45 |
| 7,407,531 B2 * | 8/2008 | Flagan et al. ................... | 95/154 |
| 2004/0009128 A1 * | 1/2004 | Rabinowitz et al. ........... | 424/46 |
| 2008/0038363 A1 * | 2/2008 | Zaffaroni ............. | A61M 11/041 424/502 |
| 2009/0000620 A1 | 1/2009 | Virr | |

FOREIGN PATENT DOCUMENTS

| | | | |
|---|---|---|---|
| CA | 2386027 A1 | 4/2001 | |
| CA | 2652216 A1 | 12/2007 | |
| DE | 38 19 988 A1 | 12/1989 | |
| DE | 195 07 410 A1 | 9/1996 | |
| DE | 19507410 A1 | 9/1996 | |
| EP | 0 119 056 A2 | 9/1984 | |
| EP | 0 734 719 A1 | 10/1996 | |
| EP | 0 764 172 A1 | 3/1997 | |
| EP | 0 794 809 A1 | 9/1997 | |
| EP | 0 877 602 A1 | 11/1998 | |
| EP | 1 522 326 A1 | 4/2005 | |
| EP | 1 790 371 A2 | 5/2007 | |

(Continued)

OTHER PUBLICATIONS

"ICRP Publication 66: Human Respiratory Tract Model for Radiological Protection, 66", Annals of the ICRP, 1994, Publication 66, vol. 24, pp. 1-3, (total of 2 pages).
J. Broadhead, et al., "Drug Development and Industrial Pharmacy", 1992, vol. 18, pp. 1169-1206.
Hsu-Chi Yeh, et al., "Models of Human Lung Airways and Their Application to Inhaled Particle Deposition", Bulletin of Mathematical Biology, 1980, vol. 42, pp. 461-480.
L. Zhang, et al., "Empirical Equations for Nasal Deposition of Inhaled Particles in Small Laboratory Animals and Humans", Aerosol Science and Technology, 1993, vol. 19, pp. 51-56.

*Primary Examiner* — Mina Haghighatian
(74) *Attorney, Agent, or Firm* — Nath, Goldberg & Meyer; Joshua B. Goldberg; Scott H. Blackman (57) ABSTRACT

The invention relates to aerosolized and humidified particles comprising a therapeutically active substance which can be obtained by suspending dry inhalable particles in a carrier gas, adding water vapor and causing condensation of water on the particles. The invention further relates to methods to generate these particles, and apparatus useful to carry out such methods.

19 Claims, 7 Drawing Sheets

(56) References Cited

FOREIGN PATENT DOCUMENTS

| | | |
|---|---|---|
| EP | 1 820 530 A1 | 8/2007 |
| JP | H06505505 A | 6/1994 |
| JP | 2003521459 A | 7/2003 |
| JP | 2010503731 A | 2/2010 |
| WO | 91/00871 A1 | 1/1991 |
| WO | 92/06703 A1 | 4/1992 |
| WO | 95/32992 A1 | 12/1995 |
| WO | 96/16689 A1 | 6/1996 |
| WO | 97/26863 A1 | 7/1997 |
| WO | 01/41854 A2 | 6/2001 |
| WO | 0228369 A1 | 4/2002 |
| WO | 03065005 A2 | 8/2003 |
| WO | 2005/097307 A1 | 10/2005 |
| WO | 2006/108558 A1 | 10/2006 |
| WO | 2009/042187 A1 | 4/2009 |
| WO | 2010037845 A1 | 4/2010 |
| WO | 2010/122103 A1 | 10/2010 |

* cited by examiner

| PKEY | x (10%) | x (16%) | x (50%) | x (84%) | x (90%) |
|---|---|---|---|---|---|
| — median diameter | 0.83 µm | 1.02 µm | 2.28 µm | 4.40 µm | 5.15 µm |
| opt. concentration: 5.05% | | | | | |
| measuring range R3: 0.5/0.9...175 µm | | | | | |

Fig. 6a

| PKEY | x (10%) | x (16%) | x (50%) | x (84%) | x (90%) |
|---|---|---|---|---|---|
| — median diameter | 0.76 µm | 0.92 µm | 2.04 µm | 3.91 µm | 4.56 µm |
| opt. concentration: 2.65% | | | | | |
| measuring range R3: 0.5/0.9...175 µm | | | | | |

Fig. 6b

HUMIDIFIED PARTICLES COMPRISING A THERAPEUTICALLY ACTIVE SUBSTANCE

This is a National Phase Application filed under 35 U.S.C. 371 as a national stage of PCT/EP2011/064399, filed Aug. 22, 2011, and claims priority from European Application No. 10173759.1, filed Aug. 23, 2010, the content of each of which is hereby incorporated by reference in its entirety.

TECHNICAL FIELD

The invention relates to aerosolized and humidified particles comprising a therapeutically active substance, methods to generate these particles, and apparatus useful to carry out such methods.

PRIOR ART

In numerous disorders and clinical situations it is desirable to introduce a therapeutically active substance into the airways of a patient, either to bring directly into contact said substance with the tissue or tissues affected by a disease (without the need of systemic administration with all its possible side effects), or in order to achieve systemic administration while bypassing the gastro-intestinal system with its potentially negative impact on the substance's stability and the relatively slow onset of the desired pharmaceutical effect.

Examples for therapeutically active substances exerting their desired effect within the tissues lining the airways are short acting beta-adrenoceptor agonists (SABA) such as Salbutamol, long acting beta-adrenoceptor agonists (LABA) such as Salmeterol or Formoterol, glucocorticoids such as Ciclesonide (all of which are used for the treatment of obstructive airway diseases, in particular COPD), and pulmonary surfactant (see below).

An example for a therapeutically active substance which, after topical administration to the airways, diffuses from the alveoli into the patient's blood stream and thus is transported to its target organ, is insulin (e.g., Pfizer's Exubera).

The most common mode of administering a therapeutically active substance to the airways is inhalation of a pharmaceutical preparation in the form of a solution, a suspension or a dry powder. Accordingly, the first step of an inhalation process is to finely disperse the pharmaceutical preparation containing the therapeutically active substance in a carrier gas, resulting in an aerosol of either droplets or solid particles. In order to make sure that an as large as possible fraction of inhaled particles is deposited in the desired section of the airways (and does not tend to impact the upper airways' walls when deposition in the deep lung is desired), it is important that the particles have the right size. More specifically it has been found that particles which are destined to be deposited upon inhalation on the nasal mucosa ideally should have a mass mean aerodynamic diameter (MMAD, see below) of at least 10 µm, while particles which are intended to enter the deep lung should have a MMAD in the range of 0.05-10 µm, preferably of 1-5 µm or even more preferably of 2-3 µm (see, e.g., ICRP, 1994. *Human respiratory tract model for radiological protection*. ICRP Publ. 66. Annals of ICRP. 24, 231 (1994); Zhang, L. and Yu, C. P. *Empirical equations for nasal deposition of inhaled particles in small laboratory animals and humans*; Aerosol. Sci. Technol. 19, 51 (1993); or Yeh, H. C. and Schum, G. M. *Models of human lung airways and their application to inhaled particle deposition*. Bull. Math. Biol. 42, 461 (1980).

Depending on the particular formulation of a therapeutically active substance to be aerosolized, different technical solutions have been devised. Liquid formulations (usually solutions or suspensions) can be aerosolized using nebulizers such as jet nebulizers, ultrasonic wave nebulizers or pressurized metered dose inhalers. DE 195 07 410 discloses the coating (micro-encapsulation) of aerosolized liquid formulations with a hydrophobic substance, wherein each droplet of the aerosol is coated with at least a monolayer of a hydrophobic C1-C18 carbonic acid or alcohol. Dry powder formulations can be aerosolized by use of dry powder inhalers (DPIs). While DPIs typically aerosolize no more than a few tens of milligrams in a single actuation, the dry powder aerosolization apparatus known from WO 2006/108558 allows the aerosolization of several grams of powdered substance in the course of a couple of minutes and thus is a good choice when large amounts (several hundred milligrams or more) of a pharmaceutical preparation are to be administered as an aerosol.

The lungs of all vertebrates contain a substance mixture called "pulmonary surfactant" or "lung surfactant". Lung surfactant has surface-active properties and reduces surface tension in the alveoli and small airways to such an extent that collapse of the alveoli during exhalation is avoided. The surface tension is regulated dynamically, so that the collapse of the alveoli and small airways in favor of the greater ones, which is to be expected according to Laplace's law, is prevented by appropriate adaptation of the surface tension. On the other hand, reduction of surface tension in the alveolar region increases pulmonary compliance (i.e., facilitates the expansion of the lung upon breathing in). All in all the presence of lung surfactant results in a well-balanced, histologically and physiologically stable structure of the lung and is vital for the normal function of this organ.

Lung surfactant is secreted by alveolar pneumocytes of type II in the form of lamellar bodies. These are compact units of phospholipid bilayers having a high proportion of dipalmitoylphosphatidylcholine (DPPC) and phosphatidylglycerol (PG). As further essential components lung surfactant contains surfactant proteins (SP) designated SP-A, SP-B, SP-C and SP-D.

SP-A is a high-molecular-weight glycoprotein which plays a decisive role in the regulation of the secretion. During the formation of the monomolecular surface film (the surfactant in a narrow sense), the hydrophobic proteins SP-C and, to a lesser extent, SP-B play the role of "thermodynamic catalysts". The presence of these proteins accelerates the spreading kinetics significantly. It is this acceleration which renders possible the adaptation of the surfactant composition to the prevailing surface tension requirements without delay. These properties are reflected in the extremely hydrophobic character of these proteins, in particular of SP-C.

While at the time of birth the lungs of mammals contain a sufficient amount of endogenous lung surfactant in order to ensure unrestrained functionality of the lungs from the first breath on, the lungs of prematurely born babies (born below 32 weeks of gestation, and especially those born below 29 weeks of gestation) are not or not sufficiently capable of producing lung surfactant, which leads to life-threatening deficiency of oxygen uptake (Infant Respiratory Distress Syndrome, IRDS). IRDS is the main cause of death in prematurely born babies.

For many years, IRDS treatment and prophylaxis has been performed rather successfully by intratracheal bolus injection of liquid lung surfactant preparations. From pilot studies it is known that lung surfactant preparations are additionally clinically effective in the case of ARDS (Adult Respiratory Distress Syndrome), including ALI (Acute Lung Injury).

Lung surfactant preparations can be obtained from the lungs of animals (e.g., sheep or cow) by a complicated extraction and centrifugation process (lung lavage or preparation from minced lung tissue), or they can be manufactured using the individual components as starting material.

WO 92/06703 describes the production of synthetic lung surfactant preparations by evaporating chloroform from a solution comprising phospholipids (such as dipalmitoylphosphatidylcholine (DPPC) and dioleylphosphatidylethanolamine (DOPE)) and cholesterol using a rotary evaporator to obtain a thin film which is resuspended in a buffer, if desired together with suitable proteins.

From WO 91/00871 it is known to concentrate an organic solution of a lung surfactant preparation containing a surfactant protein produced by gene technology, to rehydrate it using a buffer and then to lyophilize it. The resulting lyophilisate has the disadvantage, however, that it has to be rehydrated at 37° C. for 15 minutes prior to administration, which is inconvenient and prone to errors and thus not preferred by users.

EP 0 119 056 describes a process for the production of a lung surfactant preparation where all components are dissolved in an organic solvent, the resulting solution is concentrated to dryness under reduced pressure, the resulting residue is resuspended in an aqueous medium at elevated temperature over a prolonged period of time and the resulting suspension is subjected to freeze drying. This process is likewise technically very complicated.

EP 0 877 602 discloses a process for the preparation of a powdered lung surfactant preparation by spray drying solutions of all components in an organic solvent. The resulting powder has excellent properties regarding the particle size, which typically is in the range of 0.5-10 μm or even in the range of 1-5 μm, rendering the particles ideally suited for inhalation. However, in the course of animal studies involving the inhalation of dry pulmonary surfactant preparations obtained according to the procedures described in EP 0 877 602 it turned out that aerosols of such surfactant particles in normal dry medicinal air exhibit a serious "lumping" effect when entering the animals' airways. "Lumping", as used here, means the formation of large moist particle deposits on the moist surface of the tissue lining the airways. Deposits formed in the airways may reach a size that threatens to clog the bronchi, the trachea or other parts of the airways, thus posing a serious suffocation risk to the patient. Without intending to be bound by any theory, a possible explanation for this phenomenon would be that dry aerosol particles very readily stick to the airway's moist surface, leading to deposition as soon as a particle touches the airway's wall, with no particles bouncing back into the air space. Once such deposition has begun, a rapid buildup of a clog is observed. The rapid buildup might be due to a deviation from the native airways' inner geometry and hence increased deposition probability as well as to the fact that the moist surfactant deposits are not only very sticky but also firm and therefore allow for multilayer deposits to build up. In addition to the formation of deposits in the upper and lower airways, deposits may also occur within lumens through which the aerosol is conducted towards the patient's airways, including tubings and the patient interface per se. Due to their small diameter, nasal prongs (in particular those used for preterm infants) are particularly prone to deposit formation upon administration of aerosolized dry particles to be inhaled.

DESCRIPTION OF THE INVENTION

The present invention's object is to provide particles having pharmaceutical activity (i.e., a desirable activity which can be exploited for therapeutic purposes), in particular particles comprising lung surfactant and/or any other therapeutically active substance, which can be administered to a patient by inhalation and which overcome at least some of the drawbacks of the particles known from the art. More specifically, the object of the present invention is to provide inhalable particles comprising at least one therapeutically active substance, characterized in showing a significantly reduced tendency to form upon inhalation agglomerates and deposits within the patient's upper and lower airways.

Surprisingly, it has now been found that this object can be achieved by providing particles in aerosolized form which, before inhalation by the patient but after aerosolization, are subjected to a humidification step. Although the opposite might be expected, i.e. that humidified particles are more sticky and show a stronger tendency to form firm deposits ("lumps"), to the contrary it surprisingly turned out that upon inhalation an aerosol containing particles with sufficient water on their surface forms much less of firm deposits than an aerosol of essentially dry particles does.

As used in this context, "essentially dry" refers to the water content of the particles in their typical storage form of dry powders capable of being aerosolized in commercially available aerosolizers. Typically, the water content of such a dry powder (without considering chemically bound water including hydrate water) is no more than about 5% w/w, no more than about 3% w/w, no more than about 2% w/w or even no more than about 1% w/w. For example, particles of dry powder lung surfactant manufactured according to the teaching of EP 0 877 602 usually have a water content of about 2%. In general, "essentially dry inhalable particles" means inhalable particles that, when present in the form of a powder, are particles which are readily aerosolizable, in particular using one of the aerosolization devices known from the art (e.g. commercially available aerosolization devices such as Flutide® Diskus® (GlaxoSmithKline), Novopulmon® Novolizer® (Viatris), Jethaler® (Ratiopharm), Asmabec® Clickhaler® (Celltech Pharmaceuticals) or Budes® Easyhaler® (Hexal)), without a water content which would be sufficiently high to render the particles too sticky for being aerosolized, and without liquid water present which would hold together the particles by capillary forces. Prior to being suspended in a carrier gas ("aerosolized") in step (b) of the method disclosed below, the essentially dry inhalable particles form a powder. Of course it should be mentioned here that each aerosolization device has its own characteristics and limitations, and a given dry powder might be readily aerosolizable with a certain aerosolization device, while it is not efficiently aerosolizable with a different aerosolization device. Thus, in the context of this patent application, a powder of essentially dry inhalable particles means a powder which can be turned into an aerosol by at least one type of customary aerosolization device.

A "humidified" particle within the context of this patent application has a much higher water content than an essentially dry particle, which would interfere with the smooth aerosolization to individual particles (the primary particles) suspended in a carrier gas stream if aerosolization of not yet aerosolized, humidified particles was attempted.

Such humidified particles according to the present invention comprising at least one therapeutically active substance can be obtained by the steps of:

a. providing essentially dry inhalable particles comprising the at least one therapeutically active substance,
b. suspending the particles in a carrier gas to obtain a first aerosol,
c. adding water vapor to the first aerosol to obtain a second aerosol having a higher water content than the first aerosol, and
d. adjusting the temperature and/or the pressure of the second aerosol as to exceed the second aerosol's dew point and to cause condensation of water on the particles.

Accordingly, in the context of the present invention, a "humidified particle" as used herein is a particle which can be obtained by performing steps (a) to (d).

The adding water vapor to the first aerosol in step (c) to obtain the second aerosol is accomplished by either i. bringing into contact the first aerosol with a source of water vapor,
or
ii. mixing the first aerosol with a gas or gas mixture which contains water vapor, and, optionally, heating the aerosol before or during the performance of step (i) or (ii).

The first step (a) requires to provide essentially dry inhalable particles comprising at least one therapeutically active substance. "Inhalable" means that the particles can be suspended in a volume of gas (e.g., by entraining into a stream of carrier gas passing through an aerosolization chamber), can be breathed in ("inhaled") by the patient and, upon inhalation, are to a sufficiently high fraction deposited on the surfaces of the airways in order to achieve the desired therapeutic effect. Usually deposition in the lung is intended, but for certain applications it may be desired that the deposition preferentially takes place in the upper airways, for example on the nasal mucosa. For efficient delivery of inhaled particles to the deep lung it is important that the particles' aerodynamic behaviour is adjusted accordingly. Aerosolized too large or too small particles will tend to deposit on the airways' walls too early, preventing a substantial fraction of them from reaching the deep lung due to premature deposition in the upper airways. Since the particular shape of a particle, its overall size and its density have great influence on this particle's tendency to settle or impact, the concept of the aerodynamic diameter (AD) has been introduced. The aerodynamic diameter of a particle is defined as the diameter of a hypothetical sphere of unit density which has the same terminal settling velocity as said real particle, regardless of the geometric size, shape and density that particle has in reality. In order to describe an aerosol, the mass mean aerodynamic diameter (MMAD) has been defined which is the mass median of the size distribution of mass with respect to the particles' aerodynamic diameter. The MMAD can be determined according to standard DIN EN 13544-1:2007, annex C.3. In practice it turned out that an MMAD of 0.05-10 µm is suitable, and an MMAD of 1-5 µm or of 2-3 µm is optimal, for particles which are to be inhaled and whose destination is the deep lung. Particles which are destined for deposition to the nasal mucosa should have a mass mean aerodynamic diameter of 10 µm or more. Accordingly, the essentially dry inhalable particles provided in step (a) are particles that, when aerosolized, are characterized by a MMAD of 0.05-10 µm, by a MMAD of 1-5 µm or even by a MMAD of about 2-3 µm when deposition in the lung is desired, and characterized by a MMAD of 10 µm or more (e.g., a MMAD of 10-100 µm) when deposition on the nasal mucosa is intended. While upon humidification of the particles in step (d) (i.e., the deposition of condensing water on the aerosolized particles) the particles' MMAD will be slightly changed, this change will not turn a previously inhalable (dry) particle to a non-inhalable (humidified) particle with a dramatically altered MMAD which prevents deposition on the intended parts of the airways, although of course the chance of deposition of the particle may be influenced and changed to either higher or lower values. However, it is clear that if it is intended to deposit large amounts of water on the particles, the size of the essentially dry inhalable particles provided in step (a) might need to be adapted as to compensate for the change in MMAD caused by the loading of water to the particles. For example, considering the second aerosol to be by the end of step (c) at a temperature of 50° C. and to be saturated with water vapor, the aerosol would contain 83.1 g of water vapor per cubic meter. If this aerosol was cooled down in step (d) to 37° C., the saturation concentration of water vapor would be reduced to 44.0 g/m$^3$, rendering 39.1 g of water available for condensation. If the aerosol's concentration of solid particles was 20 g/m$^3$, and assuming (1) complete condensation which (2) exclusively takes place on the surface of the particles, the geometric diameter of particles having unit density would grow by about 25%.

Step (a) can be performed according to techniques known from the art. It might be possible to obtain suitable essentially dry particles of the desired size by freeze drying or by micronization (e.g., by milling, grinding or by a more advanced technique such as any of the SAS [Supercritical Anti-Solvent], the PGSS [Particles from Gas Saturated Solutions] or the RESS [Rapid Expansion of Supercritical Solutions] methods). However, it is preferred to obtain the essentially dry particles provided in step (a) by spray drying, since spray drying is a very gentle drying process for thermally sensitive materials such as certain therapeutically active substances (including peptides and proteins), results in a narrow particle size distribution and allows the particle size to be adjusted in the size range desirable for inhalation. Spray drying can be carried out in a manner known per se. This technique is described in detail in, inter alia, K. Masters, *Spray Drying Handbook*, 5th ed. 1991, and in J. Broadhead, S. K. Edmond Ronan, C. T. Rhodes, *The Spray Drying of Pharmaceuticals*, Drug Dev. Ind. Pharm. 18, 1169 (1992). The principle of spray drying is based on the atomizing a solution or suspension of the product to be dried into fine droplets which are dried in a hot gas stream. The solids which remain after the solvent has been evaporated are separated from the gas stream by means of a cyclone and/or by a filter unit and collected. For example, EP 0 877 602, the content of which herewith is incorporated by reference, teaches the spray drying of a lung surfactant preparation comprising dipalmitoylphosphatidylcholine (DPPC), palmitoyloleoylglycerophosphoglycerol ammonium salt (POPG), calcium chloride, palmitic acid and a recombinant derivative of human lung surfactant protein C (the "rSP-C" derivative), resulting in a dry lung surfactant powder having a mean particle size of 1-5 µm which is in the optimal range for inhalation of particles which are to be deposited in the lung.

The therapeutically active substance can be any substance having a desired therapeutic effect upon inhalation, including lipids such as phospholipids, small molecule drugs, peptides, proteins such as enzymes or antibodies, nucleic acids such as siRNA, and so forth. The therapeutically active substance can also be any mixture of substances which has a desired therapeutic effect upon inhalation, such as natural or artificial lung surfactant. For example, the therapeutic effect of the therapeutically active substance may be exerted by physical interaction with the lung tissue (as is the case with lung surfactant), by the binding of a molecule to a receptor, by inhibition or activation of an enzyme, by enzymatic action per se, by the binding of an antibody to a specific epitope, by RNA interference, by interacting with a pathogen present in the airways (including interaction with the pathogen's replication, toxin production and/or toxin secretion) and so forth, regardless of whether the desired therapeutic effect takes place in the lung (or other parts of the airways) already or at other locations of the body which, subsequent to inhalation and uptake, are reached by the therapeutically active substance via the vascular system. Non-limiting examples for therapeutically active substances that can advantageously be used according to the invention are both short and long acting beta-adrenoceptor agonists, glucocorticoids and other steroids (e.g., Ciclesonide), phosphodiesterase inhibitors such as, e.g., PDE4 inhibitors (in particular Roflumilast) or PDE5 inhibitors (e.g., Sildenafil), natural or artificial lung surfactant, DNAse (e.g., Pulmozyme), insulin, antibiotics, cytostatic compounds, anti-inflammatory compounds, mucolytic compounds, and any other therapeutically active substance that can advantageously be administered to the lungs of a patient. In a preferred embodiment the therapeutically active substance is lung surfactant which exerts its therapeutic effect at least in part by physical interaction with the lung tissue, namely by a reduction of the surface tension in the alveoli. In another preferred embodiment, the particle according to the invention comprises more than one therapeutically active substances. In a particularly preferred embodiment, the particle according to the invention comprises more than one therapeutically active substances, one of them being lung surfactant.

"Lung surfactant" (or "pulmonary surfactant") means any pharmaceutically acceptable substance or composition which is capable of fulfilling at least part of the normal functions of natural mammalian (in particular human) lung surfactant. Lung surfactant preparations may be obtained by extraction from natural tissues (e.g., bovine, ovine or porcine lung) or can be manufactured from individual ingredients such as phospholipids, lung surfactant proteins or derivatives thereof (including artificial lung surfactant proteins such as the KL4 polypeptide), fatty acids, salts and other components. Commercially available lung surfactants comprise Alveofact, Curosurf, Exosurf, Infasurf, Pumactant (ALEC), Surfaxin, and Survanta. At least one further lung surfactant, Venticute, has been under clinical investigation. Certain artificial lung surfactant compositions mimic natural lung surfactant by containing phospholipids and at least one recombinant derivative of surfactant protein SP-C such as the FF/I mutant called "rSP-C" (INN Lusupultide, known from EP 0 764 172), which is a truncation derivative of human SP-C which carries three point mutations. In a particularly preferred embodiment of the present invention the therapeutically active substance (or one of the therapeutically active substances, if the particles comprise more than one therapeutically active substance) is lung surfactant which has been manufactured by spray drying and comprises DPPC, POPG, rSP-C, palmitic acid, and calcium chloride. In a further particularly preferred embodiment the therapeutically active substance is lung surfactant which has been manufactured according to the teaching of EP 0 877 602.

An important application of lung surfactant is to perform at least parts of the role of natural, endogenous lung surfactant. This can be particularly important when a patient suffers from a deficiency of endogenous lung surfactant. Lung surfactant can then be administered to the patient's lungs in order to replace the missing or damaged (e.g., in case of aspiration of gastric contents, by proteolytic activity) endogenous surfactant ("surfactant replacement therapy"). Examples where the function of endogenous lung surfactant is impaired are ARDS, IRDS, idiopathic pulmonary fibrosis, cystic fibrosis, chronic obstructive pulmonary disease (COPD) (in particular COPD exacerbations), and chronic bronchitis. A further example is lung surfactant deficiency of preterm neonates (in particular of neonates born below 32 or even below 29 weeks of gestation).

However, it is to be understood that anything mentioned here regarding the therapeutically active substance(s) is meant to be an example only and shall not be construed as a limitation of the scope of the claims.

In step (b) the particles provided in (a) are detached and suspended in a carrier gas, resulting in an aerosol. The carrier gas can be any gas or gas mixture that is acceptable for inhalation by a patient. Preferably the carrier gas is air, for example medicinal air according to the European Pharmacopeia 6.3 (see below). In one embodiment, the air is enriched by oxygen. In another embodiment, the air is loaded with one or more gases selected from nitric oxide and gases having a narcotic and/or anasthetic effect. Suspending the particles in a carrier gas can be performed using a variety of techniques and aerosolization devices known from the art. For example, WO 2006/108558 discloses an aerosolization apparatus which is particularly suitable for this purpose. The particles to be suspended are stored as a powder in a reservoir and are sucked by an underpressure generated by pressure pulses into an aerosolization chamber, where they are entrained in the pulsed gas flow. This apparatus is particularly efficient and allows for the aerosolization of large amounts of powdered substances, rendering it an excellent choice for performing the present invention. In order to avoid clumping during the aerosolization process, the relative humidity of the carrier gas used to generate the first aerosol should not be too high. Preferably, the carrier gas' relative humidity is 20% or below. Even more preferred is a relative humidity which does not exceed 10%. In a particularly preferred embodiment, the gas or gas mixture used to generate the first aerosol is standardized medicinal air as is available in virtually any large hospital. Usually this air will be in conformity with the requirements for medicinal air as defined, e.g., in the European Pharmacopeia 6.3, 1238, which requires the water content of medicinal air to be no more than 67 ppm (V/V) as determined using an electric hygrometer (see also DIN EN ISO 7396-1). While the expansion of the pressurized carrier gas within the aerosolization apparatus according to WO 2006/108558, which takes place during and immediately after the aerosolization process proper, may temporarily increase the relative humidity of the carrier gas (now containing the aerosolized particles), at this stage the aerosol's relative humidity still will be far below 100%, so no condensation of water will take place. Using medicinal air for aerosol generation in step (b), the resulting first aerosol will be rather dry (i.e., will have a low relative humidity), and in order to exceed the dew point when performing step (d) the temperature and/or pressure of the aerosol would need to be drastically changed. In order to reach the goal of exceeding the dew point by more subtle changes of conditions, in step (c) water vapor is added. By this way the relative humidity can be increased from, for example, less than 20% to just below 100% (or, more generally speaking, to a value which is as close to the dew point as desired). Now, after adjusting the first aerosol's water content and, thus, its relative humidity to a high value (resulting in a "second aerosol", which corresponds to the first aerosol after water vapor has been added), only relatively small alterations of temperature and/or pressure of the aerosol are needed to exceed the dew point and, thus, to effect the onset of the desired condensation of water on the particles' surfaces.

One possibility to add water vapor to the first aerosol in step (c) to obtain the second aerosol is to mix the first aerosol with a gas or gas mixture which contains water vapor. While such mixture of the aerosol with a gas containing water vapor is relatively easy to accomplish, a disadvantage is the dilution effect. Accordingly, it would be desirable to only add water vapor to the first aerosol, without any additional carrier gas or the like. Thus, in a preferred embodiment, the first aerosol is brought into contact with a source of water vapor. "A source of water vapor" means a phase boundary at which water vapor passes from a first phase to a second phase, the second phase being the gas phase of the aerosol. In the simplest case, the first phase would be liquid water (preferably at elevated temperature to increase the water's vapor pressure), and the aerosol would flow over a certain quantity of water with the water's surface forming said phase boundary. In a preferred embodiment the liquid water is separated from the aerosol by a semi-permeable barrier which is permeable to water vapor, but essentially impermeable under the applied conditions to liquid water. Preferably the semi-permeable barrier is a membrane which usually is made from a synthetic material such as, e.g., Nafion, Goretex or Sympatex. In one embodiment, the semi-permeable barrier is made from a finely perforated material. In another embodiment, the semi-permeable barrier is made from a hydrophobic but waterpermeable material such as, e.g., silicone. In still another embodiment, the semi-permeable barrier is made from sintered material, from ceramics, or from any other material which has the desired properties in order to allow water vapor to enter the aerosol flow while retaining water in liquid form.

Accordingly, in a particularly preferred embodiment the source of water vapor according to (i) is a semi-permeable barrier, and the adding water vapor to the first aerosol is accomplished by flowing the first aerosol through the humidification chamber of a humidifier, the humidifier being characterized by said semi-permeable barrier which separates the first aerosol in the humidification chamber from water at a temperature of 37-100° C., preferably at a temperature of 45-75° C. or of 50-60° C., in a second chamber, and which semi-permeable barrier allows the passage of water vapor from the second chamber to the humidification chamber. It is further preferred that said semi-permeable barrier allows the passage of heat from the second chamber to the humidification chamber. Humidifiers comprising a semi-permeable barrier and which are useful for adding water vapor to a stream of gas to be inhaled are known from, e.g., DE 38 19 988, EP 0 794 809, EP 1 522 326, EP 1 790 371, EP 1 820 530, U.S. Pat. No. 4,773,410, US 2009/0000620, WO 01/41854, or WO 2005/097307.

Figure 3A:
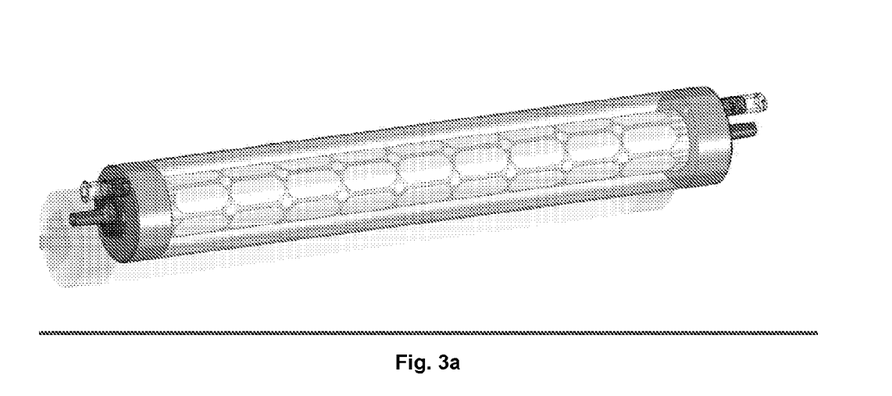
FIG. 3: Humidifier suitable for an apparatus for the preparation of particles according to the present invention.
Figure 3B:
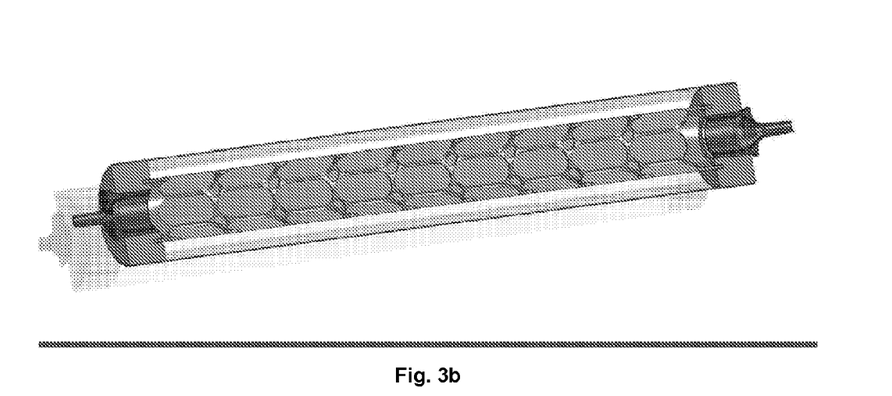

In a preferred embodiment, the humidification chamber and the second chamber containing water at elevated temperature are positioned concentrically to each other, with the second chamber encircling the tubular humidification chamber (FIG. 3). The humidifier can have a linear, rotationally symmetric configuration. However, e.g. if space constraints are to be dealt with, it is also possible to provide the humidifier in a folded configuration (e.g., having the shape of a "U") or in a helical, coiled or spiraled configuration. Usually the humidification chamber will have a length of 10-30 cm, 15-25 cm or about 20 cm. However, other lengths are conceivable as well, as long as under the particular conditions chosen the desired amount of water vapor is added to the aerosol flowing through the humidifier.

The amount of water vapor passing the phase boundary and entering the aerosol flow per time and area depends on the semi-permeable barrier's conductivity for water vapor (i.e., the ease with which water vapor can cross said barrier), on the liquid water's vapor pressure (which increases with temperature) and on the partial pressure of water vapor already present in the gas phase. In order to allow for the desired amount of water vapor to enter the gas phase flow, the temperature of the water usually will not be below 37° C. Preferably, the water temperature will be in the range of 45-75° C. or in the range of 50-60° C.

In a preferred embodiment, simultaneously to or before adding water vapor in step (c) the first aerosol is adjusted to a first temperature between 20° C. and 100° C. Usually the carrier gas employed to suspend the particles in step (b) will have a temperature close to room temperature, and the humidified aerosol will finally be administered to a patient at a temperature not significantly exceeding 37° C., but may also be about room temperature or even below. Including a heating step simultaneously to or before adding water vapor allows to transiently greatly increase the aerosol's capacity for water vapor. Accordingly, a considerable amount of water vapor can be added to the first aerosol in step (c). Once the desired amount of water vapor has been taken up (resulting in the second aerosol), the gas phase's water content usually being close to saturation, already small adjustments of temperature and/or the pressure of the aerosol are sufficient to exceed the dew point and, thus, to cause condensation of water on the particles' surface. In a preferred embodiment, this is accomplished (resulting in the onset of condensation of water on the particles) by lowering the second aerosol's temperature from a first temperature to a second temperature. In practice, heating the first aerosol to a temperature in the range of 45-75° C. or in the range of 50-60° C. turned out to be very advantageous regarding the amount of water available for condensation on the particles before administration to the patient. In a particularly preferred embodiment the condensation of water on the particles in step (d) is accomplished by heating the first aerosol before or during the addition of water vapor in step (c) to a first temperature in the range of 45-75° C. or 50-60° C. and, after having added water vapor, cooling the resulting (second) aerosol again to a second temperature in the range of 15-45° C., in the range of 18-40° C. or, even more preferably, to a second temperature of about 20° C. or about 37° C.

While the heating of the first aerosol to the first temperature can be achieved by any heating technique known from the art, it is preferred that said heating takes place simultaneously to, and is accomplished at least in part by, the addition of water vapor. The required heat can then be transported from the water phase in the humidifier to the aerosol's gas phase in part in the form of the water vapor's heat (i.e., the kinetic energy of the water molecules in the gas phase) and in part by heat conduction through the phase boundary (and, if applicable, through the semi-permeable barrier). In such a setup the humidifier, besides adding water vapor to the aerosol, serves a second function as heat exchanger, and upon leaving the humidifier the aerosol will have a greater water vapor content and will be at a higher temperature than before.

In step (d), the temperature and/or the pressure of the second aerosol are adjusted as to exceed the second aerosol's dew point. This can be achieved by different measures, which are discussed further below. Once the dew point is exceeded, water begins to condense, and the zone within the apparatus where the second aerosol's dew point is exceeded can be called "condensation zone". In general, condensation takes place wherever condensation nuclei are present, or when a very high supersaturation is reached. Due to their huge surface, aerosolized particles with a size in the micrometer range are excellent condensation nuclei. Accordingly, condensation of water from the gas phase on the surface of the aerosolized particles is a very efficient means to load water to the particles and, thus, to humidify them. This principle per se is well known from the art. In order to allow for the desired amount of water to be deposited by condensation on the aerosolized particles, the absolute amount of water vapor present in the gas phase and being capable of condensation under the conditions chosen in step (d) must be sufficiently high. The required amount of condensing water will depend, among others, on the surface of the aerosolized particles present in the condensation zone and on the desired relative water content of each single particle. It also needs to be taken into account that a certain amount of water may also condense on the walls of the condensation zone's containment (which, in a preferred embodiment, is a tubing or conduit through which the second aerosol is flowing—see below (the "second conduit")).

One possibility to exceed the dew point and to cause condensation of water on the particles is to lower the second aerosol's temperature from a first temperature to a second temperature, thus lowering the maximum amount of gaseous water which can be present in the gas phase. The second aerosol's first temperature usually will be the temperature at which the second aerosol leaves the humidifier and, thus, the second aerosol's first temperature usually is in the range of 20° C. to 100° C. It is preferred that the first temperature is in the range of 45° C. to 75° C. or in the range of 50° C. to 60° C. In a preferred embodiment, aerosolization of the particles in step (b) takes place at ambient (room) temperature, and the obtained first aerosol is heated to said first temperature during passage through the humidifier as described above. The second temperature should be sufficiently low not only to allow for the desired degree of condensation, but also to permit administration of the cooled second aerosol to a patient, without posing any discomfort or even health risk to the patient. Accordingly, the second temperature usually will be in the range of 15° C. to 45° C. More often the second temperature is in the range of 18° C. to 40° C., and preferably the second temperature is about 20° C. or about 37° C., in particular between 36° C. and 37° C.

Preferably, reducing the second aerosol's temperature from a first temperature to a second temperature is achieved by moving the second aerosol along a predetermined path within an apparatus from an area having a higher temperature to an area having a lower temperature, allowing heat to flow along the temperature gradient between the aerosol and its surrounding kept at a lower temperature. In a preferred embodiment, the predetermined path is defined by a conduit in the form of a tubing and the second aerosol flows through said tubing, the lowering of the aerosol's temperature being accomplished by a net flow of heat from the tubing's lumen to the tubing's exterior which exterior is at a lower temperature than the temperature at which the second aerosol enters the tubing. Accordingly, said tubing has dual functions: first, it serves to cool down the second aerosol to below its dew point, allowing condensation of water on the aerosolized particles to take place, and second it conducts the second aerosol from the humidifier to the patient interface from where it enters the patient's airways. "Patient interface" as used herein means any suitable interface between the device used for generation of the particles according to the invention and the patient's airways. For example, in the context of the present invention delivery devices such as face masks, nasal cannulas, nasal prongs or endotracheal tubes as known from the art can be employed as patient interface.

In a preferred embodiment, the tubing's exterior is essentially formed by ambient air having room temperature. In a second preferred embodiment, the tubing's exterior is essentially formed by a gaseous or liquid cooling medium which is adjusted to a predetermined temperature or temperature range, said medium optionally forming a countercurrent flow in relation to the aerosol flow. One example for said second embodiment would be the use of a heat exchanger having two concentrically placed compartments, one being the tubing through which the aerosol is flowing and a second one being a compartment through which a gaseous or liquid cooling medium is flowing and which surrounds the tubing along at least part of the tubing's length.

While there are no particular constraints on the tubing's exact shape, usually the tubing will be cylindrical or conical. It has been found that a length of the tubing of 40 cm to 140 cm is preferable, with a length of 70 cm to 100 cm being even more preferable. Also it was found that an inner diameter of the tubing of 1 mm to 5 mm is preferable, with an inner diameter of 3.5 mm to 4.5 mm being even more preferable. A particularly preferred tubing is essentially cylindrical, has a length of about 80 cm and an inner diameter of about 4 mm.

A flow rate of the second aerosol through the tubing of 0.2 $l \cdot min^{-1}$ to 6 $l \cdot min^{-1}$ is preferred, with a flow rate of 0.5 $l \cdot min^{-1}$ to 2 $l \cdot min^{-1}$ being even more preferred.

In order to move the second aerosol along said predetermined path from an area having a higher temperature to an area having a lower temperature (i.e., in the above preferred embodiment, to cause the aerosol flowing through said tubing), a stream of carrier gas (which preferably is air or oxygen-enriched air) can be employed. In a preferred embodiment, the apparatus used for generation of the particles according to the invention comprises in fluid flow connection with each other an inlet connected with a source of carrier gas, an aerosolization device as mentioned above (the "aerosolization unit", where the essentially dry particles are entrained in the carrier gas as to form a first aerosol), a first conduit (e.g., a tubing), a humidifier, a second conduit (e.g., a tubing) and a patient interface (or a port which allows for attachment of a patient interface in fluid flow connection with the second conduit). In this embodiment, a stream of carrier gas enters the apparatus via the inlet and, in the aerosolization unit, the essentially dry particles are entrained in this stream of carrier gas to form a first aerosol. The first aerosol then is conducted by the first conduit to the humidifier, where water vapor is added and, at the same time, the aerosol is heated to a first temperature (e.g., 50° C.-60° C.). Upon leaving the humidifier, the aerosol is at the first temperature and has a partial pressure of water vapor close to saturation (the "second aerosol"). The second aerosol leaves the humidifier via the second conduit in which it is allowed to cool down. Upon cooling, condensation of water on the particles takes place, and the essentially dry particles are individually converted to humidified particles according to the invention. After flowing through the second tubing the second aerosol reaches the patient interface from where it can be taken up ("inhaled") by the patient upon breathing in.

In general, said stream of carrier gas is caused by a pressure difference between the inlet and parts of the described apparatus which are positioned more downstream, e.g., the patient interface. In a preferred embodiment the carrier gas is provided at a pressure higher than atmospheric pressure and is drawn either directly from a compressor system (e.g., as used to provide hospitals with compressed air) or from a pressure cylinder.

Another possibility to exceed the dew point in step (d) is to reduce the second aerosol's pressure from a first pressure to a second pressure so that the aerosol's dew point is exceeded by adiabatic cooling (i.e., cooling caused by adiabatic expansion), thus lowering the maximum amount of gaseous water which can be present in the second aerosol. Preferably the second pressure will be about atmospheric pressure, since this will obviate the need of any further pressure change before the aerosol reaches the patient's airways. In one embodiment the aerosolization of the particles and the adding water vapor to the first aerosol (and, optionally, the heating of the aerosol) takes place at elevated pressure, for example at an excess pressure of $1-2\cdot10^5$ Pa. The resulting second aerosol is then expanded, for example by flowing through a nozzle into an expansion chamber which allows expansion to atmospheric pressure. In one embodiment, the expansion chamber is identical with the second conduit which connects the humidifier with the patient interface. Provided the relative humidity of the pressurized aerosol at the given temperature is sufficiently high, upon expansion of the second aerosol the dew point will be exceeded, resulting in the desired condensation of water on the particles. From the expansion chamber then the second aerosol containing the humidified particles according to the invention is conducted to the patient interface and enters the patient's airways.

Usually, the adjustment of the temperature and/or the pressure of the second aerosol required to exceed the aerosol's dew point takes place within 0.1-2 seconds, preferably within about 1 second. Accordingly, the condensation process in step (d) usually takes 0.1-2 seconds, preferably about 1 second, of time.

Figure 4A:
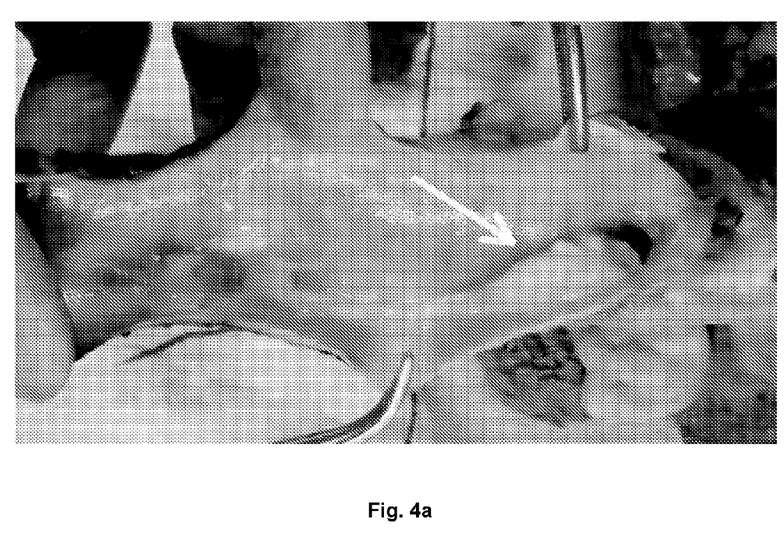
Figure 4B:
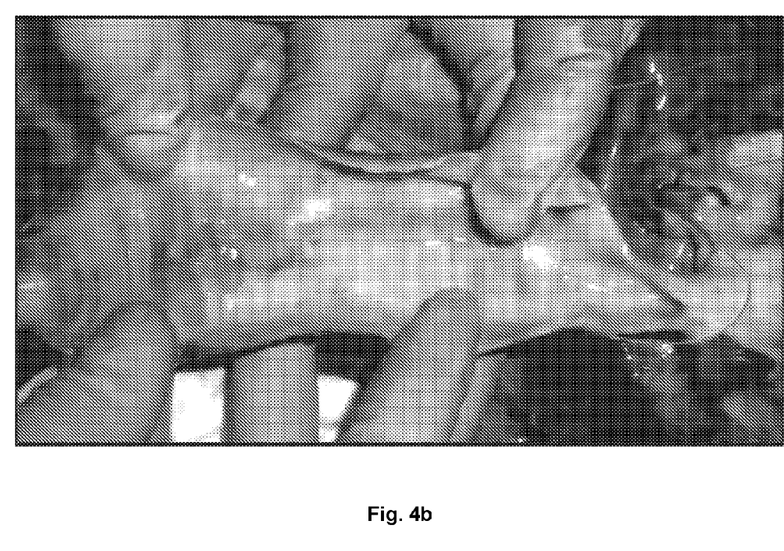

Surprisingly, the uptake of condensing water dramatically changes the tendency of the aerosolized particles to form firm deposits on surfaces of the airways to which the aerosol is administered. In an experimental study conducted to evaluate the effect on which the present invention is based, both, an aerosol of dry particles according to the art (a "non-humidified aerosol") and an aerosol of humidified particles according to the invention (a "humidified aerosol"), of a lung surfactant preparation were administered by inhalation to the airways of pigs. While administration of the non-humidified aerosol as known from the art caused large deposits in the trachea which might pose a serious threat of suffocation to a patient (FIG. 4a), after administration of an aerosol of the very same material, which, however, prior to administration had been humidified according to the invention, no deposits at all could be observed (FIG. 4b).

Accordingly, the present invention provides a number of unexpected advantages over the art:
 significantly improved safety, since the formation of deposits and clots in the patient's airways is reduced or even completely suppressed,
 improved efficiency, since virtually all aerosolized material is available for entering the lower airways and the deep lungs in finely dispersed form, without significant losses in the form of deposits and clots, and
 economic advantage, since the efforts to remove after inhalation deposits from tubings, the patient interface and the like can be minimized.

The particles according to the invention provide a highly efficient means to introduce by inhalation therapeutically active substances (or, more precisely, pharmaceutical preparations containing one or more therapeutically active substances) into the lungs of a patient, rendering them of use in therapy. In one embodiment they are used in the treatment of a disease of the respiratory system, for example IRDS (infant respiratory distress syndrome) including IRDS of premature infants, ARDS (acquired respiratory distress syndrome), COPD (chronic obstructive pulmonary disease) or CF (cystic fibrosis). A particularly preferred application of the particles according to the invention (the particles in this case comprising lung surfactant) is the use for surfactant therapy of preterm neonates having no, or not yet sufficient amounts of, endogenous lung surfactant. Preterm neonates for which such surfactant therapy is particularly advantageous are those born below 32 weeks of gestation or even born below 29 weeks of gestation. Accordingly, a further object of the present invention is a method of treatment, comprising the administration of particles as described above to the airways of a patient in need thereof.

A further object of the present invention is an apparatus for the generation of particles as described above. Such apparatus usually comprises the following elements:
(1) an aerosolization unit capable of aerosolization of essentially dry inhalable particles, the aerosolization unit having an inlet attachable to a source of carrier gas and an outlet,
(2) a humidifier comprising an inlet, a humidification chamber and an outlet, the inlet and outlet being via the humidification chamber in fluid flow connection with each other, the humidification chamber comprising a source of water vapor,
(3) either
 (3a) a patient interface having an inlet and at least one outlet, the patient interface allowing via the at least one outlet administration by inhalation of the aerosol of humidified particles to the airways of a patient, or
 (3b) a port connectable to a patient interface, the port allowing to conduct the aerosol of humidified particles to said patient interface for administration by inhalation to the patient,
(4) a first conduit connecting the outlet of the aerosolization unit with the inlet of the humidifier,
(5) a second conduit connecting the outlet of the humidifier with the inlet of the patient interface or with the port connectable to a patient interface, the second conduit allowing to adjust the temperature and/or the pressure of the aerosol.

As mentioned above, in a preferred embodiment the aerosolization unit is a device as disclosed in WO 2006/108558. It is particularly preferred that the device further has the modifications as disclosed in European patent application EP09158625.5 and the corresponding PCT application WO 2010/122103.

The humidifier has already been described above. In a preferred embodiment the humidification chamber's wall comprises a semi-permeable barrier which separates the humidification chamber from heated liquid water in a second chamber, the semi-permeable barrier allowing the passage of water vapor from the second chamber to the humidification chamber while preventing the passage of liquid water from the second chamber to the humidification chamber.

A further object of the present invention is the use of an apparatus as described above for the preparation of the particles as described above.

A further object of the present invention is the use of a spray-dried preparation of at least one therapeutically active substance for the preparation of humidified particles as described above.

A further object of the present invention is the use of a composition, the composition comprising essentially dry inhalable particles comprising at least one therapeutically active substance, for the preparation of humidified particles.

A further object of the present invention is a composition, the composition comprising essentially dry inhalable particles comprising at least one therapeutically active substance, for the preparation of humidified particles for use in therapy.

A further object of the present invention is a composition, the composition comprising essentially dry inhalable particles comprising at least one therapeutically active substance, for the preparation of humidified particles for use in the treatment of a disease of the respiratory system, for example IRDS (infant respiratory distress syndrome) including IRDS of newborn infants and IRDS of premature infants, ARDS (acquired respiratory distress syndrome), COPD (chronic obstructive pulmonary disease) or CF (cystic fibrosis).

A further object of the present invention is a commercial package or product for the preparation of humidified particles, comprising (i) essentially dry inhalable particles comprising at least one therapeutically active substance, (ii) instructions (e.g., in form of a label or package insert) to prepare humidified particles, and optionally (iii) an apparatus for preparation of humidified particles as described above.

A further object of the present invention is a method of treatment, comprising administering humidified particles to a patient in need thereof. In a preferred embodiment, said humidified particles comprise lung surfactant. In a further preferred embodiment, said patient suffers from a disease of the respiratory system, for example IRDS (infant respiratory distress syndrome) including IRDS of newborn infants and IRDS of premature infants, ARDS (acquired respiratory distress syndrome), COPD (chronic obstructive pulmonary disease) or CF (cystic fibrosis).

A further object of the present invention is a method for the generation of an aerosol of particles comprising at least one therapeutically active substance, comprising the following steps:
  a. providing essentially dry inhalable particles comprising the at least one therapeutically active substance,
  b. suspending the particles of step (a) in a carrier gas to obtain a first aerosol,
  c. adding water vapor to the first aerosol to obtain a second aerosol having a higher water content than the first aerosol, and
  d. adjusting the temperature and/or the pressure of the second aerosol as to exceed the second aerosol's dew point and to cause condensation of water on the particles.

In a particularly preferred embodiment of the invention as disclosed, the at least one therapeutically active substance comprises lung surfactant.

EXAMPLES

Example 1: Production of Spray Dried Lung Surfactant Particles 7.0 g 1,2-dipalmitoyl-3-sn-phosphatidylcholine (DPPC), 2.5 g 1-palmitoyl-2-oleoyl-3-sn-phosphatidylglycerol sodium (POPG-Na), 205 mg calcium chloride dihydrate and 250 mg palmitic acid were dissolved in 300 ml 2-propanol/water (85:15) heated to 60° C. After cooling the solution to 20° C., the solution was mixed with 350 ml of a solution of rSP-C FF/I (INN: Lusupultide) in chloroform/methanol 9:1 (c=429 mg/l). The resulting solution was spray dried using a Büchi B 191 spray drying apparatus. The drying gas was air being at 90° C. when entering the drying chamber and being at 52° C.-54° C. when leaving the drying chamber. A whitish, loose powder was obtained.

Example 2: Preparation of Humidified Aerosolized Particles

Figure 1:
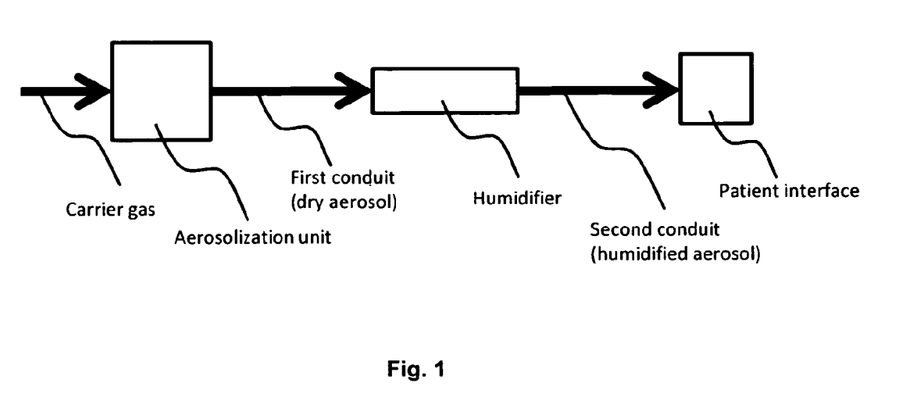
FIG. 1: Block diagram of an apparatus useful for the preparation of particles according to the present invention.
Figure 2:
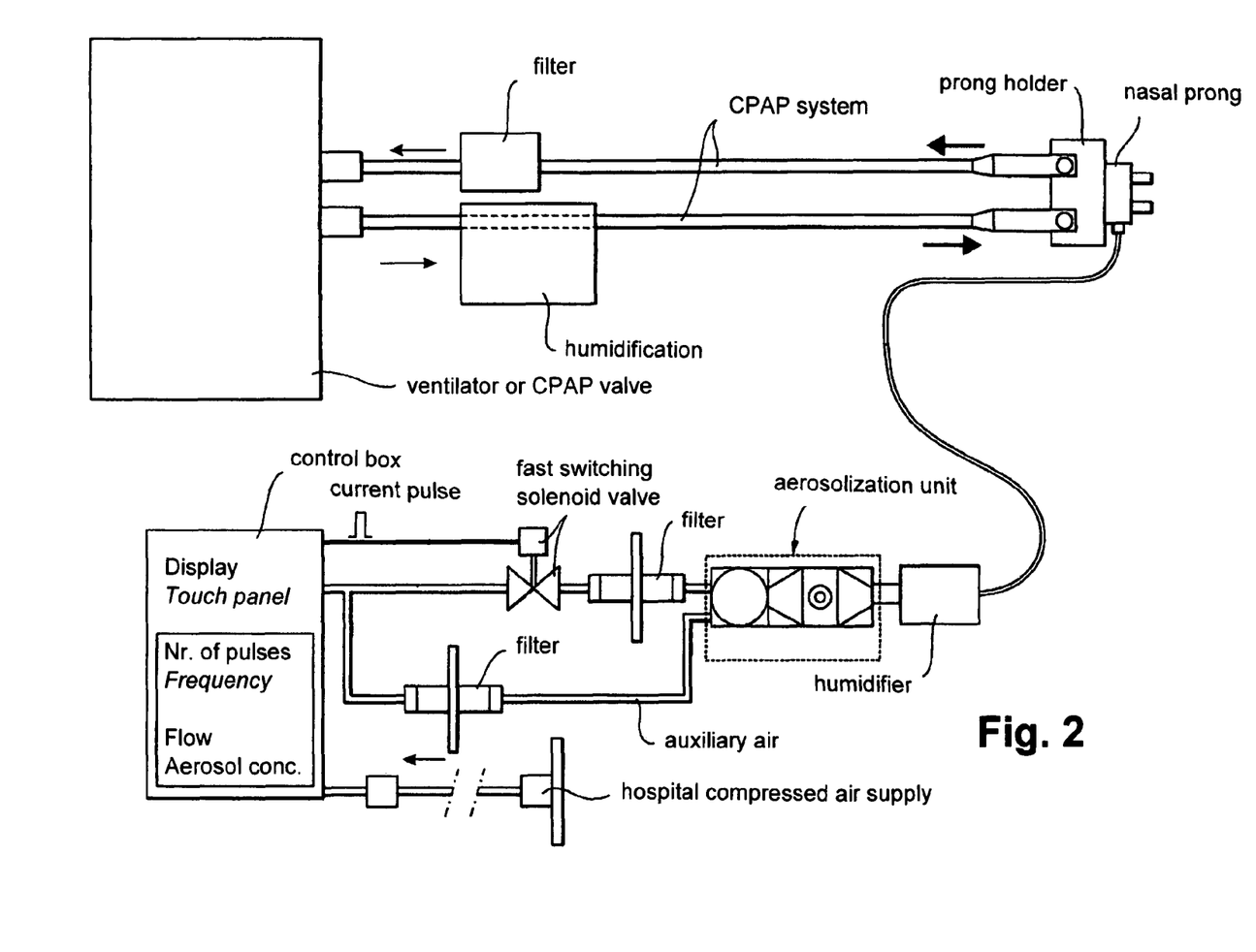
FIG. 2: Schematic diagram of a preferred embodiment of an apparatus useful for the preparation of particles according to the present invention.

Using a setup as outlined in FIG. 2, humidified lung surfactant particles were generated. Towards this, 3 grams of spray dried lung surfactant from example 1, having a mean geometric diameter of approximately 2.5 μm, were loaded into the reservoir of an aerosolization unit similar to the apparatus known from WO 2006/108558, but having the modifications as disclosed in European patent application EP09158625.5. In order to achieve aerosolization of the surfactant powder, a source of pulsed carrier gas (air) as described in WO 2006/108558, using a solenoid valve, was connected with the distal attachment portion (the inlet) of the aerosolization unit via a small sterilizing-grade filter. The proximal attachment portion of the aerosolization unit was connected to a small spacer (serving as a buffer volume to dampen the pressure pulses) with a volume of 50 ml that was continuously flushed with an additional amount of auxiliary air with a flow rate of typically 0.7 l/min. Said flow of auxiliary air was configured as to form a sheath flow along the walls of the cylindrical part of the spacer, thus ensheathing the aerosol stream entering the spacer and efficiently helping to avoid the aerosolized particles to deposit on the spacer's walls.

The air employed as carrier gas had a humidity of typically <1.8 g/m$^3$ (22° C., 1013 mbar). The source of pulsed carrier gas was adjusted to provide 10 pulses sec$^{-1}$, each pressure pulse lasting 10 msec and the pulse entering the aerosolization apparatus with a pressure of 3 bar resulting in a pulse of approx. 0.014 l/pulse when measured under standard conditions. In accordance with the principle of a jet pump, the material stored in the reservoir is sucked by an underpressure into the aerosolization channel through which the compressed carrier gas is flowing and is aerosolized. Carried by the gas stream, the aerosol then moves on into the spacer were it is further diluted by the additional carrier gas fed into the spacer. The first aerosol generated in this way had a mass concentration in the range of 5 to 25 g/m$^3$ with a flow rate typically being in the range of 0.8 to 0.9 l/min. After leaving the spacer, the pressure pulses where further dampened using a thermoplastic tube with an inner diameter of 2 mm and a length of 300 mm (the "first conduit"). Using this tube, the first aerosol was conducted to a humidifier where water vapour was added and, at the same time, the aerosol was heated. The humidifier was of the above mentioned type, comprising a tubular humidification chamber concentrically surrounded by a second chamber containing hot water at 60° C., with a semipermeable membrane forming the wall between both chambers. The humidified and heated aerosol (the "second aerosol") left the humidifier having a temperature of about 50° C. and 100% relative humidity. After leaving the humidifier, the aerosol was conducted through a flexible thermoplastic tube (the "second conduit") having an inner diameter of 4 mm, a wall thickness 1 mm and a length of 80 cm to the patient interface in the form of a set of nasal prongs. The tube was freely suspended in ambient air, thus allowing the aerosol to cool down during its way through the tube. Cooling down resulted in supersaturation of the aerosol and subsequent condensation of water on the individual aerosol particles. Given the aerosol's flow rate and the tube dimensions, the mean travelling time from the humidifier to the patient interface was about 1.4 seconds. During this time the temperature of the aerosol dropped to approx. 24° C., resulting in sufficient condensation of water vapor on the particles and therefore in an "inline" (i.e., during the passage through the condensation zone formed by the lumen of the second conduit) conversion of the essentially dry particles present in the first aerosol to humidified particles according to the invention.

Example 3: Analysis of Humidified Particles

Figure 5A:
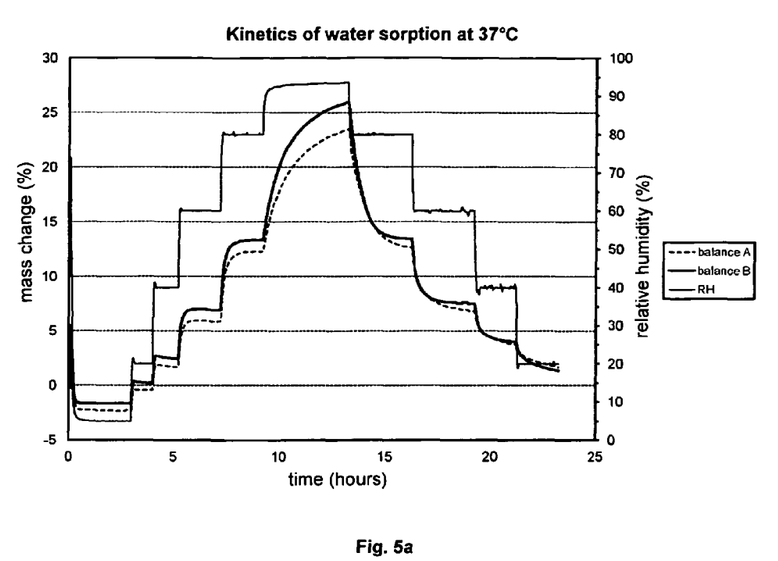
Figure 5B:
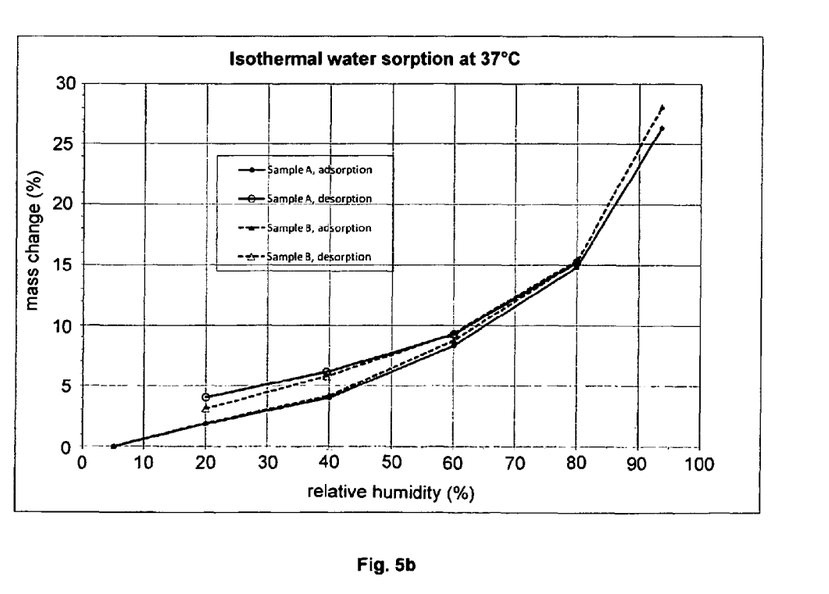
Figure 6A:
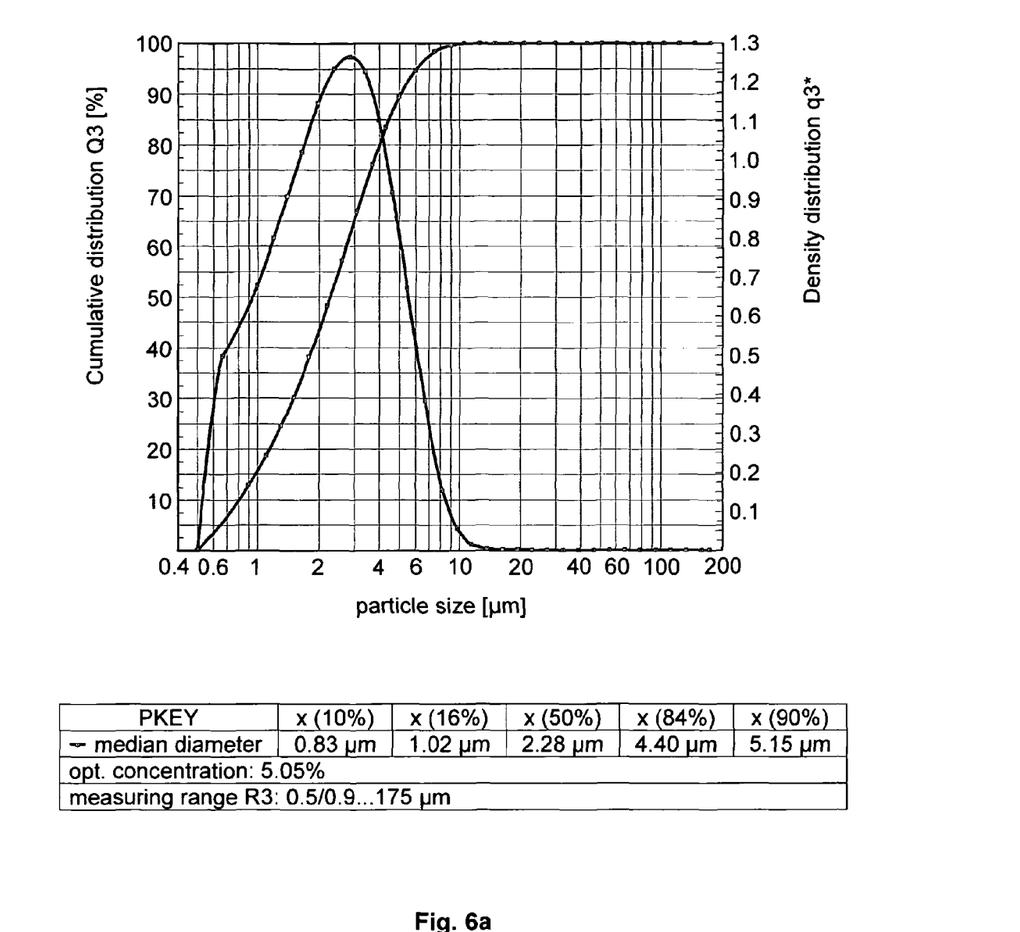
Figure 6B:
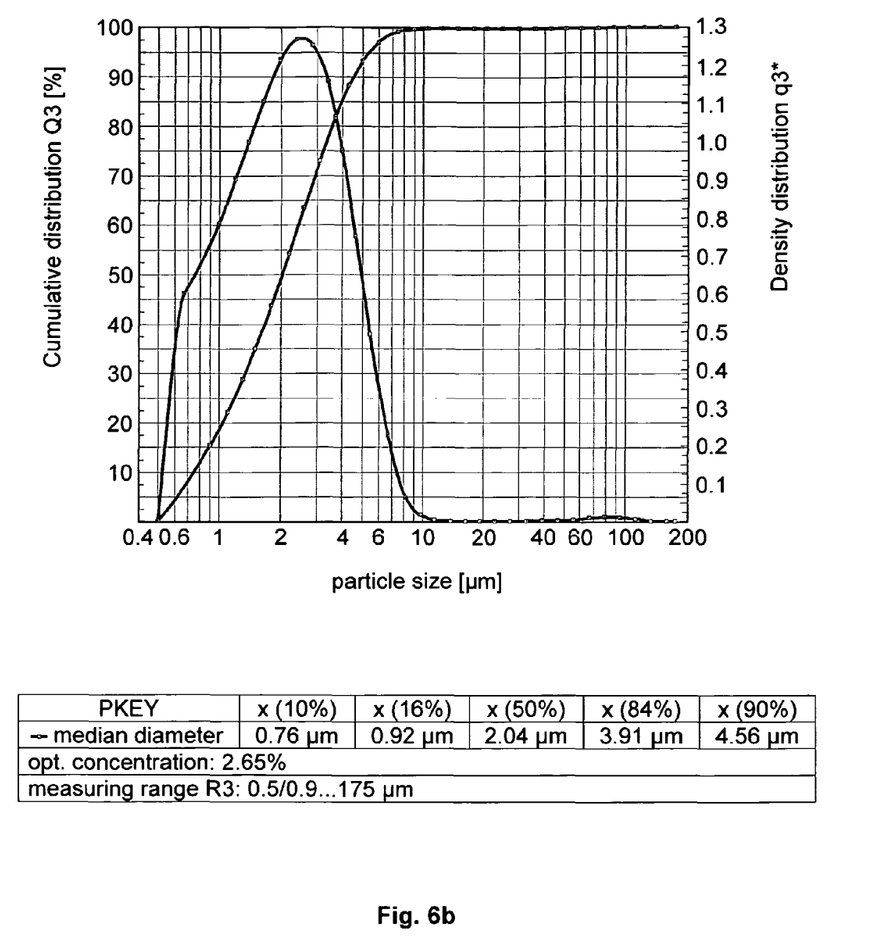

For further characterization, humidified lung surfactant particles prepared as described in Example 2 were subjected to dynamic vapor sorption and laser diffraction spectroscopy experiments.
(a) Dynamic Vapor Sorption (DVS)
In isothermal dynamic vapor sorption experiments, the mass change of a sample is measured which is exposed to varying degrees of relative moisture at a constant temperature. For an analysis of the water absorption behaviour of lung surfactant particles, a CISorp Instrument (CI Electronics, Marpiré, France) was used. Experiments were conducted in duplicate. Approx. 10 mg of dry surfactant powder obtained according to example 1 was weighed in each of the two glass pans, A and B. The glass pans were applied to the testing chamber, and the relative humidity within the testing chamber was adjusted in a stepwise fashion from 5% to 95% and then back to 20%. The temperature was kept at 37° C. during the whole experiment. The weight changes of the pans, caused by the sorption of water to the samples, were recorded and plotted against the time (and, thus, against the changes of the relative humidity). The experiments showed that the investigated particles are hygroscopic, with a weight increase of about 15% at 80% relative humidity (FIG. 5a). It also can be seen that in the range of 80% relative humidity the uptake of water is essentially reversible (FIG. 5b).
(b) Laser Diffraction Spectroscopy
The characterization of the particles was accomplished using a HELOS diffraction sensor (Sympatec, Clausthal-Zellerfeld, Germany). This well known diffraction method allows for in situ measurements of particle size distributions. The measurements where conducted either directly at the exit of the application tube (the "second conduit"), with the gas phase at 100% relative humidity, or at the exit of a 52 cm long acrylic glass tube (serving as a "drying tube") at a relative humidity well below 100%. For drying the aerosol of humidified particles, the aerosol leaving the application tube was conducted into the drying tube and mixed with dry air. While the mixture was traveling through the drying tube, the water on the particle surface evaporated giving rise to smaller particles. This shrinkage was detectable as a smaller median diameter (X50 value) of the size distribution (see below).
Comparing the volume size distribution of aerosolized dry surfactant after heating and humidification (FIG. 6a) with the same material after an additional re-drying step (FIG. 6b), it can be seen that, as expected, upon drying the particles become smaller. Humidified particles exhibited a median diameter (×50) of 2.28 μm, whereas the median diameter of re-dried particles was 2.04 μm. Assuming a spherical shape of the particles, from the observed size reduction taking into account the width of the size distribution and assuming a log normal distribution it can be estimated that, under the experimental conditions chosen in Example 2, the essentially dry particles of step (a) of the present invention, after aerosolization in step (b), take up by condensation in step (d) an amount of water corresponding to approximately 40% of their dry weight. From the observation that the particles are capable of absorbing water corresponding to approximately 15% of their dry weight (see Example 3a) it can be concluded that the humidified particles prepared in Example 2 are characterized by a water film coating the particles' surfaces which corresponds to roughly 25% (40%−15%=25%) of the particles' dry weight, once equilibrium is reached (i.e., once a particle has absorbed as much water as possible under the given conditions). Since it is not known how long it takes to reach equilibrium, it is safe to say that, under the chosen conditions, upon leaving the second conduit (and, thus, upon potentially entering the patient's airways) the humidified particles are covered by a water film corresponding to between about 25% and about 40% of their dry weight.

FIGURES

FIG. 4: Opened tracheae of pigs treated with dry lung surfactant aerosol (FIG. 4a) and with humidified lung surfactant aerosol according to the invention (FIG. 4b). A large deposit (arrow) and several minor deposits can be easily seen in the trachea of the pig treated with dry aerosol, while no deposits are visible in the trachea of the animal treated with humidified aerosol according to the invention.

FIG. 5: Dynamic vapor sorption (DVS) analysis of lung surfactant particles. In FIG. 5a, mass change at 37° C. is plotted against time, upon stepwise changes of relative humidity. The two curves represent duplicate experiments. In FIG. 5b, the thus obtained mass changes are plotted against relative humidity. Closed circles indicate mass changes upon increasing relative humidity, open circles represent mass changes upon subsequent decreasing relative humidity.

FIG. 6: Volume size distribution analysis by laser diffraction spectrometry of humidified lung surfactant particles, before (FIG. 6a) and after (FIG. 6b) re-drying as described in Example 3b.

The invention claimed is:
1. Aerosolized particles ready for administration to a patient needing such administration, comprising at least one therapeutically active substance and obtained by the following steps:
   a. providing essentially dry inhalable particles comprising the at least one therapeutically active substance, the essentially dry inhalable particles having a first desired mass mean aerodynamic diameter (MMAD) suitable for an intended administration to a patient, b. suspending the particles of step (a) in a carrier gas to obtain a first aerosol with aerosolized essentially dry inhalable particles at the first MMAD, c. adding water vapor to the first aerosol to obtain a second aerosol having a higher water content than the first aerosol, and d. adjusting the temperature and/or the pressure of the second aerosol as to exceed the second aerosol's dew point and to cause condensation of water on the particles, so as to increase the first MMAD of the aerosolized particles to a second MMAD, which second MMAD remains suitable for the intended administration, wherein the at least one therapeutically active substance includes lung surfactant.

2. Particles according to claim 1, wherein the adding water vapor to the first aerosol in step (c) to obtain the second aerosol is accomplished by either i. bringing into contact the first aerosol with a source of water vapor, or ii. mixing the first aerosol with a gas or gas mixture which contains water vapor, and, optionally, heating the aerosol before or during the performance of step (i) or (ii).

3. Particles according to claim 2, wherein the source of water vapor in step (i) is a semi-permeable barrier, and the adding water vapor to the first aerosol is accomplished by flowing the first aerosol through the humidification chamber of a humidifier, the humidifier being characterized by said semi-permeable barrier which separates the first aerosol in the humidification chamber from water at a temperature of 37-100° C. in a second chamber, and which semi-permeable barrier allows the passage of water vapor and optionally the passage of heat, but blocks the passage of liquid water, from the second chamber to the humidification chamber.

4. Particles according to claim 1, wherein in step (d) the second aerosol's dew point is exceeded by lowering the second aerosol's temperature from a first temperature to a second temperature.

5. Particles according to claim 4, wherein the second aerosol's first temperature is between 20° C. and 100° C.

6. Particles according to claim 4, wherein the second aerosol's second temperature is between 15° C. and 45° C.

7. Particles according to claim 4, wherein step (d) is characterized by the second aerosol moving with a flow rate along a predetermined path within an apparatus from an area having a higher temperature to an area having a lower temperature.

8. Particles according to claim 7, wherein the predetermined path is defined by a tubing and the second aerosol flows through said tubing, the lowering of the second aerosol's temperature being accomplished by a net flow of heat from the tubing's lumen to the tubing's exterior which exterior is at a lower temperature than the temperature at which the aerosol enters the tubing, the tubing being cylindrical or conical, the tubing's length being either between 40 cm and 140 cm, between 70 cm and 100 cm or about 80 cm, and the tubing's inner diameter being either between 1 mm and 5 mm, between 3.5 and 4.5 mm or about 4 mm.

9. Particles according to claim 7, wherein the second aerosol's flow rate is selected from either 0.2-6 $l \cdot min^{-1}$ or 0.5-2 $l \cdot min^{-1}$.

10. Particles according to claim 1, wherein the adjustment of the temperature and/or the pressure of the second aerosol in step (d) required to exceed the aerosol's dew point takes place within 0.1-2 seconds.

11. A method of treating a disease of the respiratory system in a patient, wherein the disease is selected from the group consisting of IRDS (infant respiratory distress syndrome), IRDS of newborn infants, IRDS of premature infants, ARDS (acquired respiratory distress syndrome), COPD (chronic obstructive pulmonary disease) and CF (cystic fibrosis), comprising administering to said patient by inhalation of a therapeutically effective amount of the particles according to claim 1.

12. A composition comprising the particles according to claim 1.

13. An apparatus for the generation of particles according to claim 1, the apparatus comprising (1) an aerosolization unit capable of aerosolization of essentially dry inhalable particles, the aerosolization unit having an outlet and, if appropriate via an inlet, being in fluid flow connection with a source of carrier gas, (2) a humidifier comprising an inlet, a humidification chamber and an outlet, the inlet and outlet being via the humidification chamber in fluid flow connection with each other, the humidification chamber comprising a source of water vapor, (3) a patient interface having an inlet and at least one outlet, the patient interface allowing via the at least one outlet administration by inhalation of the aerosol of humidified particles to the airways of a patient, (4) a first conduit connecting the outlet of the aerosolization unit with the inlet of the humidifier, (5) a second conduit connecting the outlet of the humidifier with the inlet of the patient interface, the second conduit allowing to adjust the temperature and/or the pressure of the second aerosol.

14. A method for generating the aerosolized particles of claim 1, comprising the following steps: a. providing essentially dry inhalable particles comprising the at least one therapeutically active substance, b. suspending the particles of step (a) in a carrier gas to obtain a first aerosol, c. adding water vapor to the first aerosol to obtain a second aerosol having a higher water content than the first aerosol, and d. adjusting the temperature and/or the pressure of the second aerosol as to exceed the second aerosol's dew point and to cause condensation of water on the particles.

15. A commercial package or product for preparation of the aerosolized particles of claim 1, comprising (i) the essentially dry inhalable particles comprising at least one therapeutically active substance as required by step a. in claim 1, (ii) instructions to prepare aerosolized particles according to the steps listed in claim 1, and optionally (iii) an apparatus for the generation of said aerosolized particles as set forth in claim 1.

16. The particles of claim 1, wherein each of the first and second MMAD is suitable for inhalation by the patient and deposition in the patient's lung.

17. The particles of claim 16, wherein each of the first and second MMAD is between 0.05-10 μm.

18. The particles of claim 1, wherein each of the first and second MMAD is suitable for inhalation by the patient and deposition on the patient's nasal mucosa.

19. The particles of claim 18, wherein each of the first and second MMAD is at least 10 μm.

* * * * *